(12) United States Patent
Rubin et al.

(10) Patent No.: US 10,258,277 B2
(45) Date of Patent: Apr. 16, 2019

(54) METHOD AND SYSTEM FOR DETERMINING FRACTIONAL FAT CONTENT OF TISSUE

(71) Applicant: ENDRA Life Sciences Inc., Ann Arbor, MI (US)

(72) Inventors: Jonathan M. Rubin, Ann Arbor, MI (US); Michael M. Thornton, London (CA); Aghapi Mordovanakis, Ann Arbor, MI (US)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 16/009,021

(22) Filed: Jun. 14, 2018

(65) Prior Publication Data

US 2019/0038220 A1 Feb. 7, 2019

Related U.S. Application Data

(62) Division of application No. 15/666,546, filed on Aug. 1, 2017, now Pat. No. 9,888,880.

(51) Int. Cl.
*A61B 5/00* (2006.01)
*A61B 8/08* (2006.01)
*A61B 8/00* (2006.01)

(52) U.S. Cl.
CPC .......... *A61B 5/4872* (2013.01); *A61B 5/0035* (2013.01); *A61B 5/0095* (2013.01);
(Continued)

(58) Field of Classification Search
CPC .. H05K 999/99; A61B 5/4872; A61B 5/0035; A61B 5/0095; A61B 5/4244;
(Continued)

(56) References Cited

U.S. PATENT DOCUMENTS

| 4,385,634 A | 5/1983 | Bowen |
| 5,713,356 A | 2/1998 | Kruger |

(Continued)

OTHER PUBLICATIONS

S. B. Reeder and C. Sirlin, "Quantification of liver fat with magnetic resonance imaging," Magn Reson Imaging Clin N Am vol. 18, No. 3, pp. 337-357, Aug. 2010.

(Continued)

*Primary Examiner* — Bo Joseph Peng
(74) *Attorney, Agent, or Firm* — Stanley E. Jelic

(57) ABSTRACT

A system and method for determining fractional fat content of tissue comprises registering thermoacoustic image coordinates to an acquired ultrasound image, the acquired ultrasound image at least comprising target tissue within a region of interest; defining a thermoacoustic voxel grid coincident with the region of interest; obtaining thermoacoustic image measurement values from tissue within the region of interest corresponding to the voxels within the defined thermoecoustic voxel grid to yield a thermoacoustic measurement matrix; normalizing the thermoacoustic image measurement values within the thermoacoustic measurement matrix; calculating a fractional fat content map for the target tissue within the region of interest based on the normalized thermoacoustic image measurement values within the thermoacoustic measurement matrix and a reference thermoacoustic measurement value; and correcting the fractional fat content map based on tissue speed-of-sound data to yield a final fractional fat content map for the target tissue within the region of interest.

20 Claims, 11 Drawing Sheets

(52) U.S. Cl.
CPC .......... *A61B 5/4244* (2013.01); *A61B 5/7246* (2013.01); *A61B 5/7485* (2013.01); *A61B 8/0858* (2013.01); *A61B 8/4416* (2013.01); *A61B 8/469* (2013.01); *A61B 8/5223* (2013.01); *A61B 8/5261* (2013.01); *H05K 999/99* (2013.01)

(58) Field of Classification Search
CPC ... A61B 5/7246; A61B 5/7485; A61B 8/5261; A61B 8/0858; A61B 8/4416; A61B 8/469; A61B 8/5223
See application file for complete search history.

(56) References Cited

U.S. PATENT DOCUMENTS

| | | | |
|---|---|---|---|
| 9,706,977 | B2 | 7/2017 | Manohar et al. |
| 9,757,092 | B2 * | 9/2017 | Oraevsky .............. A61B 8/5215 |
| 9,888,879 | B1 | 2/2018 | Cho et al. |
| 9,888,880 | B1 | 2/2018 | Cho et al. |
| 9,980,677 | B1 | 5/2018 | Cho et al. |
| 2012/0197117 | A1 | 8/2012 | Picot et al. |
| 2013/0301380 | A1 * | 11/2013 | Oraevsky .............. A61B 8/5215 367/7 |
| 2015/0250388 | A1 * | 9/2015 | Arbabian ............. A61B 8/0833 600/424 |

OTHER PUBLICATIONS

M. P. Andre et al., "Accurate diagnosis of nonalcoholic fatty liver disease in human participants via quantitative ultrasound", 2014 IEEE International Ultrasonics Symposium, 204, pp. 2375-2377, 2014.
O. W. Hamer et al., "Fatty liver: Imaging patterns and pitfalls", Radiographics, vol. 26, No. 6, pp. 1637-1653, 2006.
D. A. Sass, P. Cang, and K. B. Chopra, "Nonalcoholic fatty liver disease: a clinical review," Dig. Dis. Sci., vol. 50, No. 1, pp. 171-180, Jan. 2005.
M. F. Xia et al., "Standardized ultrasound hepatic/renal ratio and hepatic attenuation rate to quantify liver fat content: an improvement method", Obesity, vol. 20, No. 2, pp. 444-452, 2012.
D. R. Bauer et al., "Spectroscopic thermoacoustic imaging of water and fat composition," Appl. Phys. Lett., vol. 101, 2012.
X. Wang et al., "Microwave-induced thermoacoustic imaging model for potential breast cancer detection," IEEE Trans. Biomed. Eng., vol. 59, No. 10, pp. 2782-2791, Oct. 2012.
T. J. Allen et al., "Spectroscopic photoacoustic imaging of lipid-rich plaques in the human aorta in the 740 to 1400 nm wavelength range", J. Biomed. Opt., vol. 17, No. 6, Jun. 2012.
L. Pan et al., "Differentiating fatty and non-fatty tissue using photoacoustic imaging," Proc. of SPIE vol. 8943, 2014.
G. Xu et al., "Functional Pitch of a Liver: Fatty Liver Disease Diagnosis with Photoacoustic Spectrum Analysis," Proc. of SPIE vol. 8943, 2014.
C. Tian et al., "Imaging and sensing based on dual-pulse nonlinear photoacoustic contrast: a preliminary study on fatty liver," Optics Letters, vol. 40, No. 10, pp. 2253-2256, May 2015.
G. Ku and L. V. Wang, "Scanning thermoacoustic tomography in biological tissue," Med. Phys., vol. 27, No. 5, pp. 1195-1202, May 2000.
G. J. Diebold and T. Sun, "Properties of photoacoustic waves in one, two, and three dimensions," Acta. Acust. united. Ac., vol. 80, No. 4, pp. 339-351, Jul. 1994.
X. L. Dean-Ben, "On the link between the speckle free nature of optoacoustics and visibility of structures in limited-view tomography," Photoacoustics, vol. 4, No. 4, pp. 133-140, Jul. 2016.
C. Gabriel et al., "The dielectric properties of biological tissues: I. Literature survey," Med. Phys., vol. 41, No. 11, pp. 2231-2249, Nov. 1996.
S. Gabriel et al., "The dielectric properties of biological tissues: II. Measurements in the frequency range 10 Hz to 20 GHz," Med. Phys., vol. 41, No. 11, pp. 2251-2269, Nov. 1996.
S. K. Ng et al., "Determination of added fat in meat paste using microwave and millimetre wave techniques," Meat Science, vol. 79, No. 4, pp. 748-756, Aug. 2008.

* cited by examiner

METHOD AND SYSTEM FOR DETERMINING FRACTIONAL FAT CONTENT OF TISSUE

FIELD

The subject disclosure relates to methods and systems for determining fractional fat content of tissue.

BACKGROUND

The prevalence of obesity has been on the rise in the U.S. and the rest of the developed world for the last few decades. It is widely believed that obesity increases the risk of fat infiltration in, and accumulation around vital organs (heart, liver, kidney, pancreas, etc.), resulting in an inflammatory response that may lead to organ dysfunction and failure. Moreover, it is believed that as much as 14% of men and 12% of women within the normal body-mass index (BMI) range (20-25 kg/m$^2$) have disproportionate fat build-up in and around abdominal organs. Infiltrated and visceral fat deposits have been associated with an increased risk of diabetic and cardiovascular diseases. Further, non-alcoholic steatohepatitis (NASH) has a clear association with hepatocellular cancer.

The most reliable non-invasive methods for the assessment of fat distribution and the quantification of visceral fat deposits involve magnetic resonance imaging (MRI) and computed tomography (CT) imaging. Similarly, proton magnetic resonance spectroscopy ($^1$H-MRS) is considered to be the gold standard for the measurement of infiltrated (ectopic) fat in liver, muscle, heart and pancreas tissues, and has been validated against needle biopsies. Unfortunately, these techniques are not cost effective, and are usually not prescribed for a general body-fat composition assessment.

There are strong indications that the ectopic fat composition in the body (i.e. the visceral fat to subcutaneous fat ratio) and the percentage of fat infiltration in specific organs (liver, heart, pancreas) are strong predictors for metabolic and cardiovascular diseases. Early detection and intervention can slow disease progress, resulting in a more favorable prognosis. However, practical and cost-effective methods for the quantitative evaluation of ectopic fat composition do not exist.

Thermoacoustic imaging is an imaging modality that adds new insights into properties of tissues and other objects, above those offered by other established imaging modalities. Specifically, thermoacoustic imaging provides information related to the thermoelastic properties of tissue.

Unlike conventional ultrasound imaging, thermoacoustic imaging offers the advantage of an endogenous contrast for fat and fatty tissues due to their starkly lower electrical conductivity and permittivity in the radio frequency (RF) range compared to other water-rich soft-tissues.

The lower absorption coefficient in fat and fatty tissues compared to lean soft tissues, results in a strong contrast in the thermoacoustic absorption image that makes the fat regions appear darker compared to lean soft tissues.

Although techniques for determining fractional fat content of tissue have been considered, improvements are desired. It is therefore an object at least to provide novel methods and systems for determining fractional fat content of tissue.

SUMMARY

It should be appreciated that this summary is provided to introduce a selection of concepts in a simplified form that are further described below in the detailed description. This summary is not intended to be used to limit the scope of the claimed subject matter.

In one aspect there is provided a method for determining fractional fat content of tissue comprising: registering thermoacoustic image coordinates to an acquired ultrasound image, the acquired ultrasound image at least comprising target tissue within a region of interest; defining a thermoacoustic voxel grid coincident with the region of interest; obtaining thermoacoustic image measurement values from tissue within the region of interest corresponding to the voxels within the defined thermoacoustic voxel grid to yield a thermoacoustic measurement matrix; normalizing the thermoacoustic image measurement values within the thermoacoustic measurement matrix; calculating a fractional fat content map for the target tissue within the region of interest based on the normalized thermoacoustic image measurement values within the thermoacoustic measurement matrix and a reference thermoacoustic measurement value; and correcting the fractional fat content map using tissue speed-of-sound data to yield a final fractional fat content map for the target tissue within the region of interest.

In some embodiments, the calculating and correcting are performed iteratively. For example, during the correcting a corrected thermoacoustic measurement matrix is generated based on the tissue speed-of-sound data. The corrected thermoacoustic measurement matrix and the reference thermoacoustic measurement value are used to recalculate the fractional fat content map, and the above steps are repeated until the final fractional fat content map for the target tissue is generated. The calculating and correcting may be performed iteratively a threshold number of times or until the change in one or more values from one iteration to the next falls below a threshold.

In one embodiment, the corrected thermoacoustic measurement matrix is generated by scaling the thermoacoustic measurement values within the thermoacoustic measurement matrix by a cubed ratio, and wherein the ratio is the speed of sound in the reference tissue divided by the speed of sound in the target tissue.

In some embodiments, during the normalizing the thermoacoustic measurement values within the thermoacoustic measurement matrix are normalized as a function of radio frequency energy, attenuation and the number of voxels in the thermoacoustic voxel grid.

In some embodiments, the reference thermoacoustic measurement value is derived from lean tissue as compared to the target tissue. The target tissue within the region of interest may for example be one of liver tissue, pancreatic tissue, muscle tissue, lung tissue and heart tissue and the lean tissue may for example be one of kidney tissue, portal vein tissue and gallbladder bile.

In some embodiments, an ultrasound imaging system is used to acquire the ultrasound image and the region of interest is delineated on the acquired ultrasound image. The delineated region of interest may encompass the target tissue and reference tissue from which the reference thermoacoustic measurement value is derived.

In some embodiments, calculating the fractional fat content map is further based on energy absorption values of the target tissue and the reference tissue. Calculating the fractional fat content map may be further based on heat capacity of the target tissue and the reference tissue. Alternatively, in some embodiments calculating the fractional fat content map is based on a comparison of previously-generated data that maps fractional fat content to thermoacoustic measurements for the target tissue.

In some embodiments, the final fractional fat content map may be used to grade the target tissue.

In another aspect there is provided an apparatus comprising: a thermoacoustic imaging system configured to acquire thermoacoustic image data of target tissue within a region of interest; and one or more processors configured to: register coordinates of the thermoacoustic image data to an acquired ultrasound image, the acquired ultrasound image comprising the target tissue; define a thermoacoustic voxel grid coincident with the region of interest; generate from the thermoacoustic image data, a thermoacoustic measurement matrix comprising thermoacoustic measurement values that correspond to the voxels within the defined thermoacoustic voxel grid; normalize the thermoacoustic image measurement values within the thermoacoustic measurement matrix; calculate a fractional fat content map for the target tissue within the region of interest based on the normalized thermoacoustic image measurement values within the thermoacoustic measurement matrix and a reference thermoacoustic measurement value; and correct the fractional fat content map based on tissue speed-of-sound data to yield a final fractional fat content map for the target tissue within the region of interest.

BRIEF DESCRIPTION OF THE DRAWINGS

Embodiments will now be described more fully with reference to the accompanying drawings in which.

DETAILED DESCRIPTION

Figure 1:
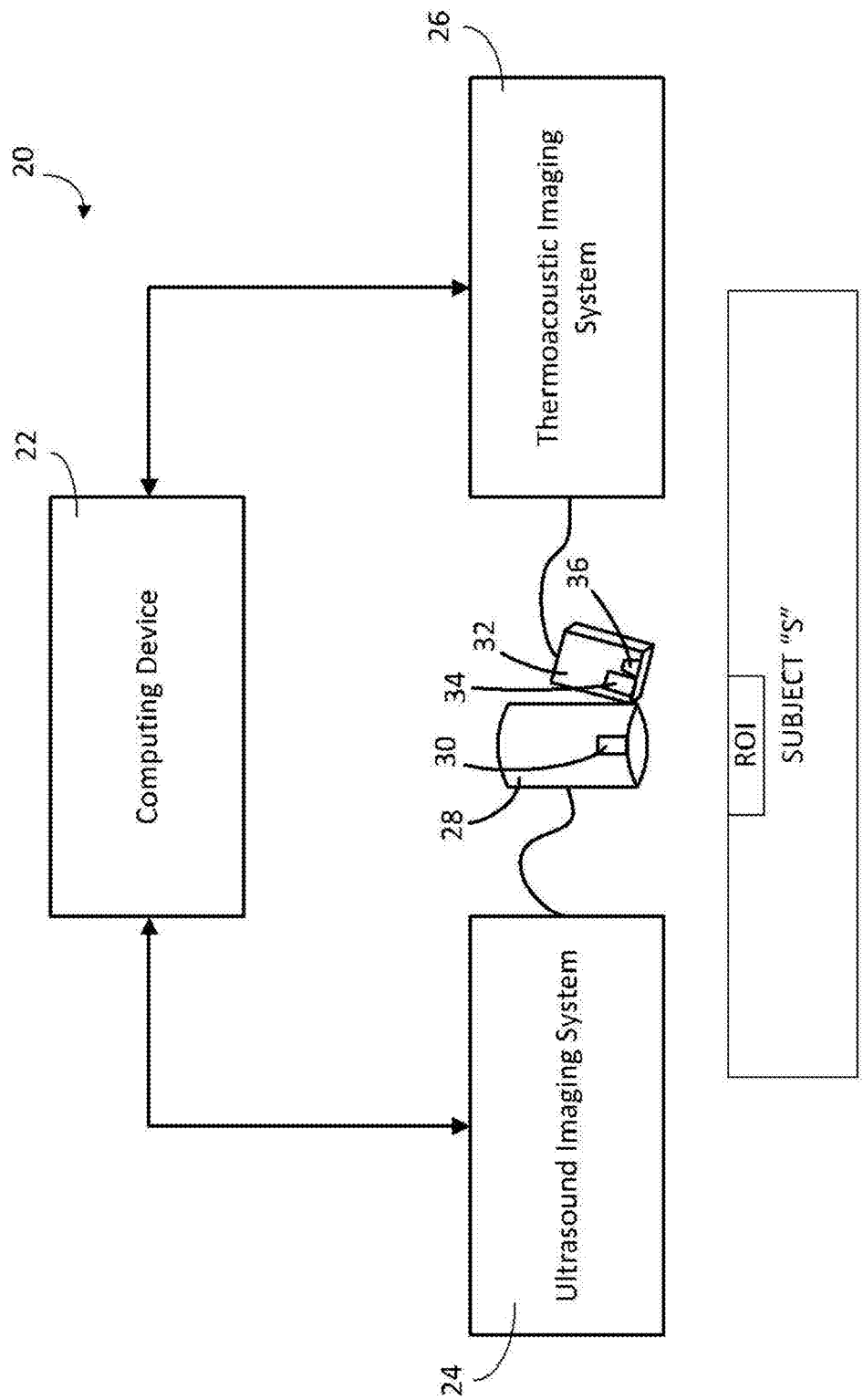
FIG. 1 is a schematic diagram of a system for determining fractional fat content of tissue.

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including by not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientation depicted in the figures.

The subject disclosure describes methods for determining fractional fat content in tissue. For example, the subject disclosure describes methods for quantifying ectopic fat content in tissues with fatty infiltration such as the liver, pancreas, or muscles (such as the heart). Specifically, the methods described herein rely on thermoacoustic imaging to obtain a thermoacoustic image of tissue within a region of interest of a subject with the aim of quantifying fractional fat content of the tissue within the region of interest. Also, the methods described herein rely on ultrasound imaging to navigate to and locate the region of interest.

The subject disclosure also describes systems for determining fractional fat content of tissue. Specifically, the systems described herein comprise a thermoacoustic imaging system for obtaining a thermoacoustic measurement or thermoacoustic image of the tissue within the region of interest. In some embodiments, a pulsed radio-frequency (RF) source of electromagnetic radiation is used to deliver energy to the tissue and excite the thermoacoustic effect. The RF source may have a frequency between 10 MHz and 100 GHz and a pulse duration between 0.1 nanosecond and 10 microseconds. Other embodiments may use a pulsed source of visible or infrared radiation with a wavelength between 400 nanometers and 10 micrometers and a pulse duration between 10 picoseconds and 10 microseconds.

In embodiments of the above methods and systems, the tissue analyzed is selected, without limitation, from the liver, pancreas, heart, kidney, lung, esophagus, thymus, breast, prostate, brain, muscle, nervous tissue, epithelial tissue, bladder, gallbladder, intestine, spleen, stomach, testes, ovaries, uterus, skin and adipose tissues allowing fat infiltration into these tissues to be determined and assessed.

Fat-containing tissue regions having a lower absorption for radio frequency waves result in a weaker thermoacoustic signal. In some embodiments, pixel-intensity-based image segmentation methods are employed to delineate fat and fatty-tissue segments within the thermoacoustic image, resulting in a segmented fat image. A single intensity threshold or multiple intensity thresholds may be used to segment the thermoecoustic image. The segmentation intensity threshold(s) may be determined by a trained operator selecting representative "fat" and "non-fat" pixels with a pointing device or may be determined by an algorithm based on the known ratio of thermoacoustic signal magnitude for both fat and lean tissues. In other embodiments, sophisticated algorithms such as morphological transforms or histogram equalization can be used to enhance the contrast of the thermoacoustic image prior to segmentation.

Embodiments may require that the segmented thermoacoustic image be registered to the ultrasound image. For embodiments where the thermoacoustic and ultrasound images are both acquired using the same transducer element array, image registration becomes simple as both images are defined with respect to the coordinate system of the transducer element array. Alternatively, for embodiments where two or more transducer element arrays having a known geometric relationship to one another are used, image registration can be performed by a transform that maps the coordinate system of the ultrasound transducer element array to that of the thermoacoustic transducer element array. Alternatively, image registration may also be performed by imaging a known phantom with well-defined reference points (at least three fiducial markers) that show up in both imaging modalities. The transform that maps these fiducial markers from one imaging modality to another can then be used to register the thermoacoustic and ultrasound images to one another without prior knowledge of the transducer element array geometry.

In one embodiment, the thermoacoustic data is analyzed to construct a quantitative and geometrically-accurate image of fat and fatty-tissue distribution in and around organs of interest. This fat image can be analyzed to quantify the volume, thickness, and distribution of visceral fat deposits around a specific organ of interest (e.g. heart, lungs, liver, pancreas etc.).

In some embodiments, the averaged thermoacoustic signal from a region of interest within a specific tissue is obtained and analyzed to compute the fractional ectopic fat content within the region of interest. Quantitative visceral and ectopic fat distribution data can be used along with other clinical data to diagnose disease, monitor the progress of disease, assess the efficacy of a treatment plan, and more broadly compute the patient's risk profile for a certain disease of interest.

The methods described herein are suited to environments where images and data of subjects are acquired in a time sequence, as to construct a time evolution representation of the tissue volume or structure of interest over periods ranging from one second to several months or years.

Embodiments of the above systems may include an energy coupling system to direct and couple the electromagnetic radiation to the subject and induce the thermoacoustic effect in the tissue within the region of interest. The energy coupling system may comprise a thermoacoustic transducer having one or more transducer element arrays to detect and record the acoustic signals generated from the thermoacoustic effect. In further embodiments, some or all of the transducer element arrays may double as conventional ultrasound transceivers, which can emit and receive acoustic waves for conventional ultrasound imaging. In further embodiments, additional transceiver element arrays may be incorporated within the energy coupling system to transmit and receive ultrasonic waves for conventional ultrasonic imaging. It will be appreciated by those of ordinary skill in the art that the one or more transducer element arrays may comprise a single transducer element, a linear or curved one-dimensional transducer element array, a two-dimensional transducer element array or a sparse array of transducer elements. The energy coupling system may require a gel-like material or a water capsule to interface to the subject with suitable impedance matching for both ultrasound and electromagnetic radiation.

Embodiments of the above systems may further comprise electronic circuits and components designed to record, amplify, filter and digitize signals detected by the one or more transducer element arrays and a computing device comprising one or more processors such as a central processing unit (CPU) etc. to perform thermoacoustic and ultrasonic image reconstruction.

In separate embodiments, the obtained thermoacoustic data can be a single volume measurement, a two-dimensional image, or a three-dimensional reconstruction of the region of interest.

Particular non-limiting examples of systems and methods for determining fractional fat content of tissue will now be described.

Turning now to FIG. 1, an exemplary system for determining fractional fat content of tissue is shown and is generally identified by reference numeral 20. As can be seen, the system 20 comprises a programmed computing device 22 communicatively coupled to an ultrasound imaging system 24 and to a thermoacoustic imaging system 26. The ultrasound imaging system 24 and thermoacoustic imaging system 26 are configured to obtain ultrasound image data and thermoacoustic image data, respectively, of a subject S that at least includes a region of interest ROI within the subject S. The region of interest ROI encompasses target tissue within the subject to be examined to determine the fractional fat content thereof.

The programmed computing device 22 in this embodiment is a computer or other suitable processing device comprising, for example, one or more processors, system memory (volatile and/or non-volatile memory), other non-removable or removable memory (e.g., a hard disk drive, RAM, ROM, EEPROM, PROM, CD-ROM, DVD, flash memory, etc.) and a system bus coupling the various computer components to the one or more processors. The computing device 22 may also comprise networking capabilities using Ethernet, Wi-Fi, Bluetooth™ and/or other suitable network formats, to enable wired and/or wireless connection to shared or remote drives, one or more networked computers, or other networked devices. One or more input devices, such as a mouse, a keyboard, a touch pad, etc. (not shown) are coupled to the computing device 22 for receiving operator input. A display device (not shown), such as one or more computer screens or monitors, is coupled to the computing device 22 for displaying one or more generated images that are based on ultrasound image data received from the ultrasound imaging system 24 and/or thermoacoustic image data received from thermoacoustic imaging system 26. The display device may be a touch-sensitive display device allowing the display device to act as an input device as well.

The ultrasound imaging system 24 comprises an ultrasound transducer 28, housing one or more transducer element arrays 30. The ultrasound transducer 28 is configured to emit sound waves into the subject S including the region of interest ROI. The sound waves directed into the subject S echo off tissue within the subject S, with different tissues reflecting varying degrees of sound. These echoes are received by the one or more transducer element arrays 30 of the ultrasound transducer 28 and are processed by electronic circuits and components of the ultrasound imaging system 24 to record, amplify, filler and digitize the echoes before being communicated as ultrasound image data to the computing device 22 for further processing and for presentation on the display device and subsequent interpretation by the operator. In this embodiment, the ultrasound imaging system 24 utilizes B-mode ultrasound imaging assuming a nominal speed of sound of 1,540 m/s. As ultrasound imaging systems are known in the art, further specifics of the ultrasound imaging system 24 will not be described further herein.

The thermoacoustic imaging system 26 comprises a thermoacoustic transducer 32 that houses one or more transducer element arrays 34 as well as a radio-frequency (RF) source 36. The RF source 36 is configured to generate short pulses of RF electromagnetic radiation that are directed into the subject S including the region of interest ROI to deliver energy to tissue within the subject S and excite the thermostatic effect. The energy delivered to the tissue induces acoustic pressure waves that are detected by the thermoacoustic imaging system 26 using the one or more transducer element arrays 34 of the thermoacoustic transducer 32. In this embodiment, the RF source 38 has a frequency between about 10 Mhz and 100 Ghz and has a pulse duration between about 0.1 nanoseconds and 10 microseconds. Acoustic pressure waves detected by the one or more transducer element arrays 34 are processed by electronic circuits and components of the thermoacoustic imaging system 26 to record, amplify, filer and digitize the acoustic pressure waves before being communicated as thermoacoustic image data to the computing device 22 for further processing and for presentation on the display device and subsequent interpretation by the operator. As thermoacoustic imaging systems are known in the art, further specifics of the thermoacoustic imaging system 26 will not be described further herein.

The computing device 22 in this embodiment comprises programmed instructions, that when executed by the one or more processors, enable the computing device 22 to process acquired thermoacoustic image data to allow fractional fat content of target tissue within the region of interest ROI to be determined so that the tissue within region of interest ROI can be graded.

Figure 2:
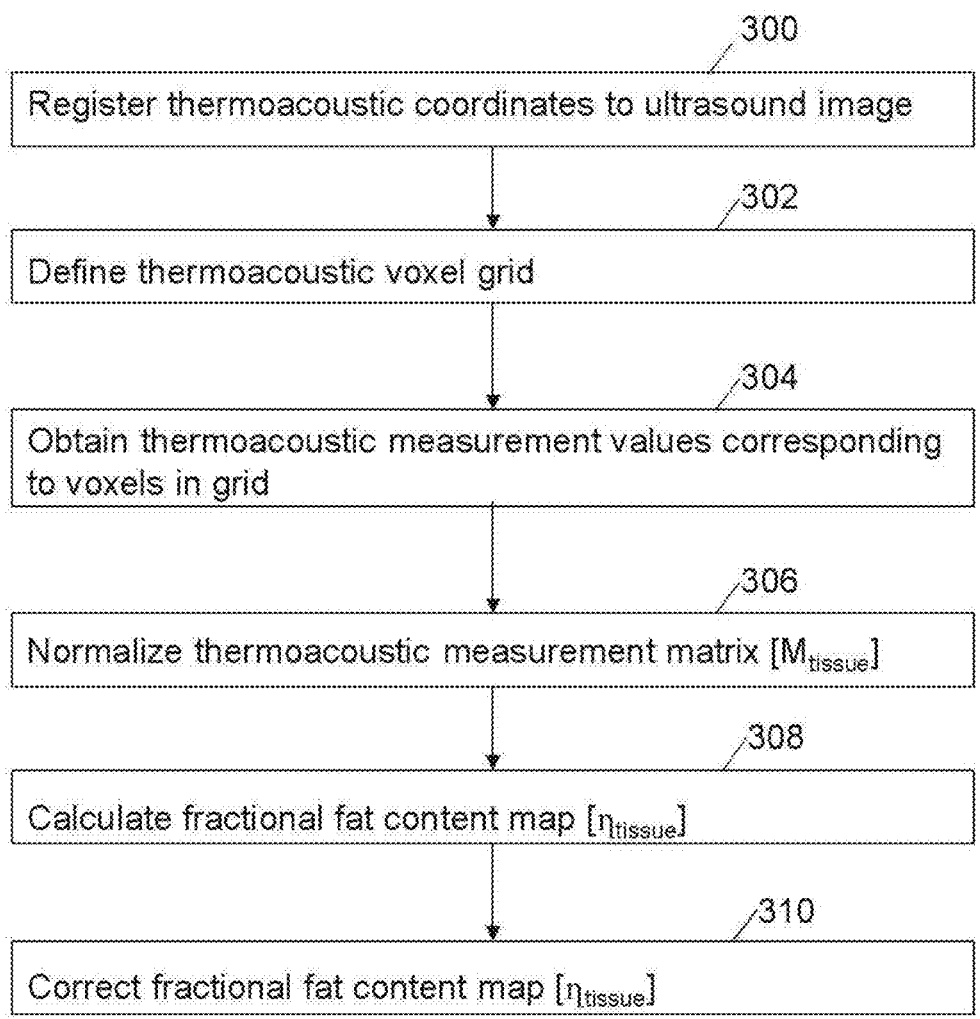
FIG. 2 is a flowchart showing a method for determining fractional fat content of tissue.

Turning now to FIG. 2, the general method performed to determine the fractional fat content of the tissue within region of interest ROI is shown. During the method, thermoacoustic image coordinates are registered to an acquired ultrasound image (step 300). The acquired ultrasound image at least comprises the tissue within the region of interest ROI. A thermoacoustic voxel grid coincident with the region of interest ROI is defined (step 302) and thermoacoustic image measurement values from the tissue within the region of interest ROI corresponding to the voxels within the defined thermoacoustic voxel grid are obtained to yield a thermoacoustic measurement matrix (step 304). The thermoacoustic image measurement values within the thermoacoustic measurement matrix are normalized (step 306) and a fractional fat content map for the target tissue within the region of interest ROI based on the normalized thermoacoustic image measurement values within the thermoacoustic measurement matrix and a reference thermoacoustic measurement value are calculated (step 308). The fractional fat content map is then corrected based on tissue speed-of-sound data to yield a final fractional fat content map for the target tissue within the region of interest ROI (step 310).

Figure 3:
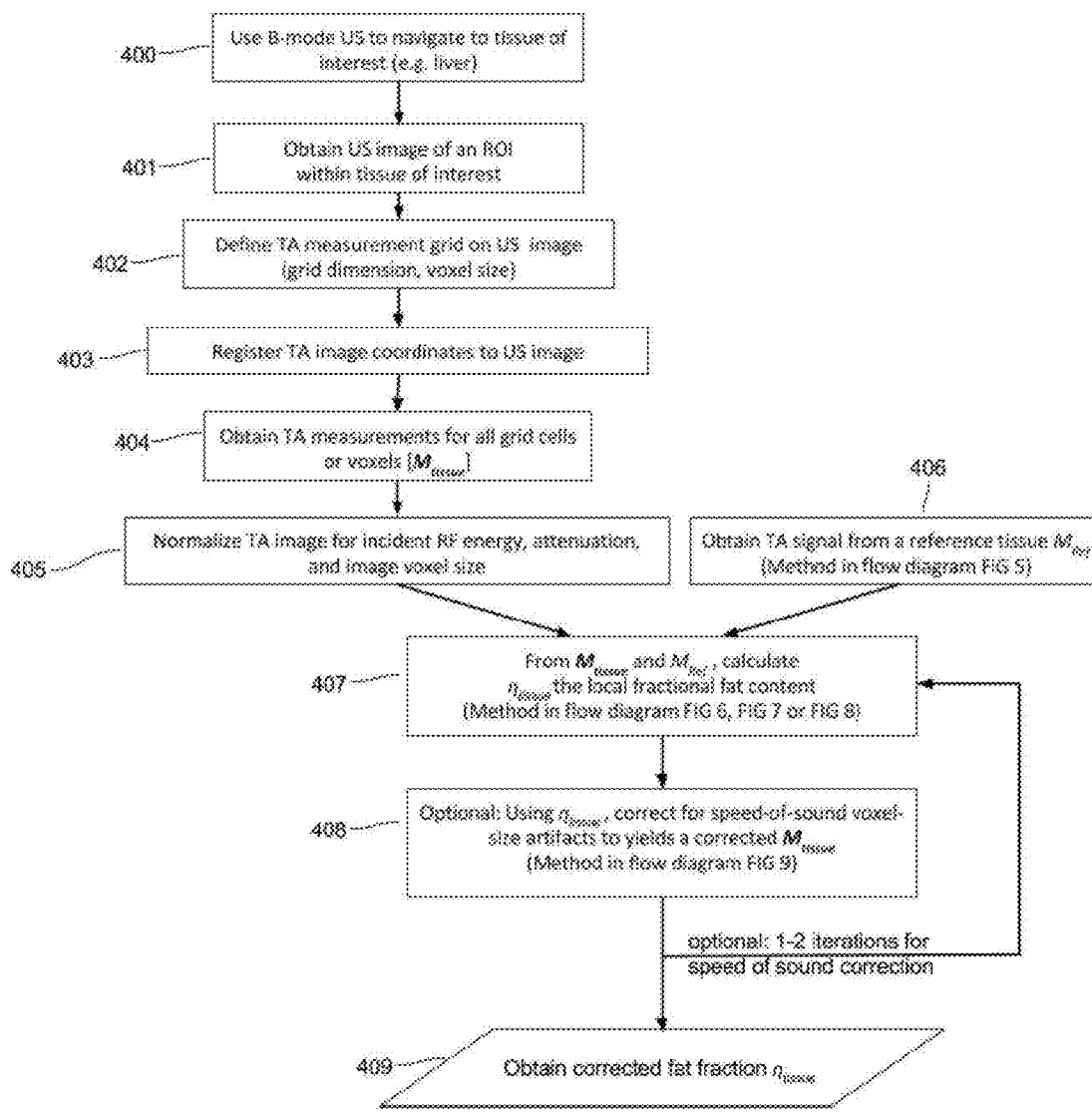
FIG. 3 is another flowchart showing the method for determining fractional fat content of tissue.

FIG. 3 better illustrates the method for determining the fractional fat content of the tissue within the region of interest ROI. Initially, the ultrasound imaging system 24 is used to image the subject S using the ultrasound transducer 28. During this step, ultrasound image data obtained by the ultrasound imaging system 24 is communicated to the computing device 22. The ultrasound image data is processed by the computing device 22 and a reconstructed ultrasound image is presented on the display device. This allows the operator to move the ultrasound transducer 28 over the subject S to navigate to the region of interest ROI within the subject (step 400).

Once the region of interest ROI within the subject S has been located, an ultrasound image of tissue of the subject S at least including the region of interest ROI is obtained (step 401). The region of interest ROI delineates a plurality of voxels of the ultrasound image. The region of interest ROI may be rectangular, elliptical or other geometric or non-geometric shape and may encompass an entire organ of the subject S, a portion of an organ, or other tissue or vasculature within the subject. The region of interest ROI may also encompass reference tissue of the subject S as will be described. The region of interest ROI may be designated by the operator via an input device or through interaction with the display device if the display device is a touch-sensitive display device. Alternatively, the region of interest ROI may be designated by the computing device 22 automatically through execution of programmed instructions based on known anatomy and the tissue's ultrasound properties (e.g. reflectivity, elasticity, etc.).

The thermoacoustic imaging system 26 is then used to image the subject S using the thermoacoustic transducer 32. During this step, thermoacoustic image data obtained by the thermoacoustic imaging system 26 is communicated to the computing device 22. The thermoacoustic image data is processed by the computing device 22 to generate a thermoacoustic image of the tissue of the subject S including the region of interest ROI.

A thermoacoustic (TA) measurement or voxel grid is then defined on the acquired ultrasound image (step 402). During this step, the size and position of the thermoacoustic measurement grid are defined so that the thermoacoustic measurement grid corresponds in size and position to (i.e. is coincident with) the region of interest ROI. The unit-cell or voxel arrangement of the thermoecoustic measurement grid is also defined. In this embodiment, the voxel arrangement of the thermoacoustic measurement grid may comprise a single voxel covering the entire region of interest ROI or may be an array of voxels.

The coordinates of the thermoacoustic image are then registered to the coordinates of the ultrasound image (step 403). In this embodiment where the one or more transducer element arrays 30 and 34 of the ultrasound transducer 28 and the thermoacoustic transducer 32, respectively, have a known geometric relationship to one another, image registration is performed using a transform that maps the coordinate system of the one or more transducer element arrays 30 of the ultrasound transducer 28 to the one or more transducer element arrays 34 of the thermoacoustic transducer 32. For embodiments where the thermoecoustic and ultrasound images are both acquired using the same transducer element array, image registration becomes simple as both images are defined with respect to the coordinate system of the transducer element array. Alternatively, image registration may be performed by imaging a known phantom with well-defined reference points (at least three fiducial markers) that show up in both the ultrasound and thermoacoustic imaging modalities. A transform that maps these fiducial markers from one imaging modality to the other can then be used to register the ultrasound and thermoacoustic images to one another without prior knowledge of the transducer element array geometry.

Next, a thermoacoustic image of tissue of the subject S at least including the region of interest is obtained. During this stage, for each defined voxel of the thermoacoustic measurement grid, a thermoacoustic measurement value $M_{tissue}$ is obtained (step 404) resulting in a thermoacoustic measurement matrix $[M_{tissue}]$. Depending on the defined voxel arrangement of the thermoacoustic measurement grid and hence, the size and position of the defined voxels, for each defined voxel, thermoacoustic signal values generated in response to acoustic pressure waves returned by target tissue within the defined voxel are averaged to yield the thermoacoustic measurement value $M_{tissue}$ for the defined voxel. If the thermoacoustic measurement grid comprises a single voxel, all of the thermoacoustic signal values returned by the target tissue within the region of interest ROI selected at step 400 are averaged to yield a single thermoacoustic measurement value $M_{tissue}$ for the thermoacoustic measurement matrix $[M_{tissue}]$.

The thermoacoustic measurement values of the thermoacoustic measurement matrix $[M_{tissue}]$ are then normalized taking into account RF energy, attenuation and the size of the voxels of the thermoacoustic measurement grid.

In order to quantify the fractional fat content of tissue within the region of interest ROI, a reference thermoacoustic measurement value $M_{ref}$ based on thermoacoustic signal values from reference tissue, typically tissue of the subject S with a known thermoacoustic absorption coefficient, is required (step 406). The reference tissue may be selected from one of a number of sources. For example, the reference tissue may be (i) the bile in the gallbladder or the common duct; (i) the portal vein; (iii) kidney tissue; (iv) spleen; or (v) other tissue known to be lean.

Figure 4:
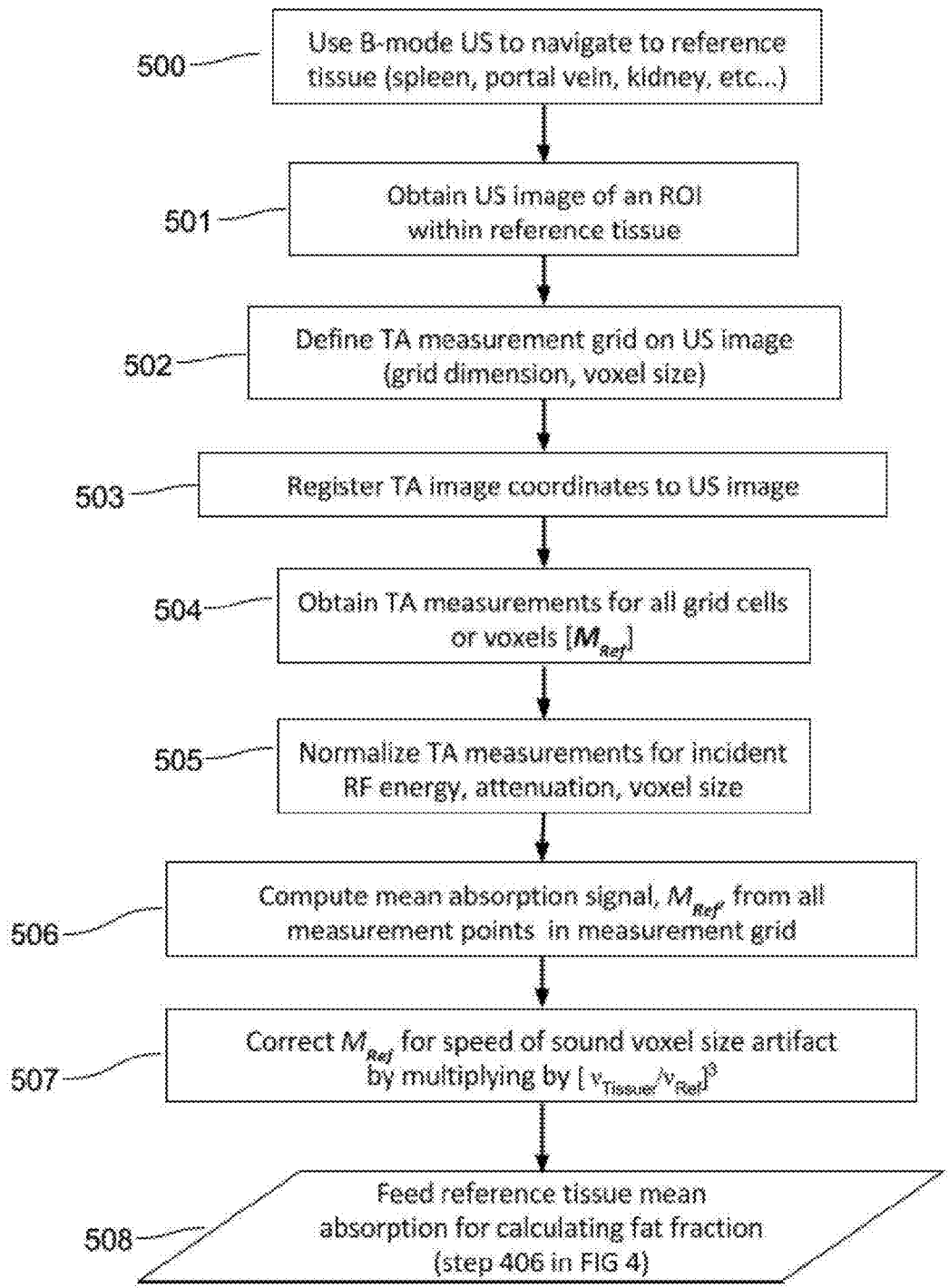
FIG. 4 is flowchart showing a method for determining a reference thermoacoustic measurement value.

Turning now to FIG. 4, the steps carried out to generate the reference thermoacoustic measurement value $M_{ref}$, are shown. As will be appreciated, these steps are similar to those performed in order to generate the thermoacoustic measurement matrix $[M_{tissue}]$. Initially, the ultrasound imaging system 24 is used to image the reference tissue using the ultrasound transducer 28. During this step, ultrasound image data obtained by the by the ultrasound imaging system 24 is communicated to the computing device 22. The ultrasound image data is processed by the computing device 22 and a reconstructed ultrasound image is presented on the display device. This allows the operator to move the ultrasound transducer 28 over the subject S to navigate to the reference tissue within the subject (step 500).

An ultrasound image of the reference tissue including a region of interest ROI thereof is obtained (step 501). The thermoacoustic imaging system 26 is then used to image the subject S using the thermoacoustic transducer 32. During this step, thermoacoustic image data obtained by the thermoacoustic imaging system 28 is communicated to the computing device 22. The thermoacoustic image data is processed by the computing device 22 to generate a thermoacoustic image of the reference tissue within the region of interest ROI.

A thermoacoustic measurement grid is then defined on the acquired ultrasound image (step 502). During this step, the size and position of the thermoacoustic measurement grid are defined so that the thermoacoustic measurement grid corresponds in size and position to the region of interest ROI. The unit-cell or voxel arrangement of the thermoacoustic measurement grid is also defined. In this embodiment, the voxel arrangement of the thermoacoustic measurement grid may comprise a single voxel covering the entire region of interest ROI or may be an array of voxels.

The coordinates of the thermoacoustic image are then registered to the coordinates of the ultrasound image (step 503). In this embodiment where the one or more transducer element arrays 30 and 34 of the ultrasound transducer 28 and the thermoacoustic transducer 32, respectively, have a known geometric relationship to one another, image registration is performed using the transform that maps the coordinate system of the one or more transducer element arrays 30 of the ultrasound transducer 28 to the one or more transducer element arrays 34 of the thermoacoustic transducer 32.

Next, a thermoacoustic image of the reference tissue within the region of interest ROI is obtained. During this stage, for each defined voxel of the thermoacoustic measurement grid, a thermoacoustic measurement value $M_{ref}$ is obtained (step 604) resulting in a reference thermoacoustic measurement matrix $[M_{ref}]$. Depending on the defined voxel arrangement of the reference thermoacoustic measurement grid, for each defined voxel, thermoacoustic signal values generated in response to acoustic pressure waves returned by reference tissue within the defined voxel are averaged to yield the thermoacoustic measurement value $M_{ref}$ for the defined voxel.

The thermoacoustic measurement values $M_{ref}$ of the reference thermoacoustic measurement matrix $[M_{ref}]$ are then normalized taking into account RF energy, attenuation and the size of the voxels of the reference thermoacoustic measurement grid (step 560).

The mean thermoacoustic measurement value $M_{ref}$ based on the thermoacoustic measurement values $M_{ref}$ within the reference thermoacoustic measurement matrix $[M_{ref}]$ is then computed (step 506).

Since the thermoacoustic measurements of the reference thermoacoustic measurement matrix $[M_{ref}]$ are typically taken from reference tissue that differs from the target tissue within the region of interest ROI selected in step 400, and since the reference tissue may differ from the tissue within the region of interest ROI selected in step 400 in terms of acoustic properties (e.g. speed of sound), a correction or scaling factor needs to be applied to account for voxel size difference due to sound speed difference. For instance, if the target tissue within the region of interest ROI selected in step 400 is from the liver (speed of sound 1,590 m/s) and the reference tissue is from the bile in the gallbladder, the mean thermoacoustic measurement value $M_{ref}$ has to be scaled by $[v_{Liver}/v_{Gallbladder}]^3$, where $v_{Liver}$ and $v_{Gallbladder}$ are the speed of sound in the liver and gallbladder bile, respectively (step 507). The normalized and scaled mean thermoacoustic measurement value $M_{ref}$ is then used in step 406 in order to determine fractional fat content of the tissue within the region of interest ROI selected in step 400 (step 508).

Figure 5:
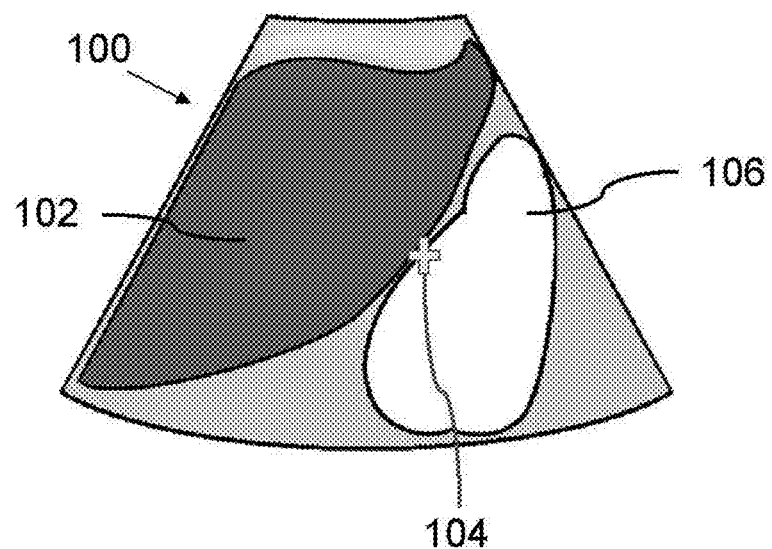
FIG. 5 is an ultrasound image of tissue to be examined to determine fractional fat content together with reference tissue and showing a region of interest encompassing the tissue to be examined and the reference tissue.

If desired, steps 400 and 600 can be performed concurrently allowing the same ultrasound image to be used at steps 401 and 501. For example, FIG. 5 shows an ultrasound B-mode image 100 in which both the liver 102 and kidney 106 of the subject S are prominent. Region of interest 104 is shown encompassing a portion of the subject's liver 102 that is to be examined to determine fractional fat content. The region of interest 104 also encompasses a portion of the subject's kidney 106 (reference tissue) from which the reference thermoacoustic measurement value $M_{ref}$ is generated.

As will be appreciated, when the same ultrasound image is used at steps 401 and 501, a single region of interest ROI that encompasses both the tissue region for which the fractional fat content is to be determined and the reference tissue can be used allowing a single thermoacoustic measurement grid to be defined and used at steps 402 and 602. Also, only one thermoacoustic image that at least encompasses the single region of interest ROI can be used at steps 404 and 604.

Figure 6:
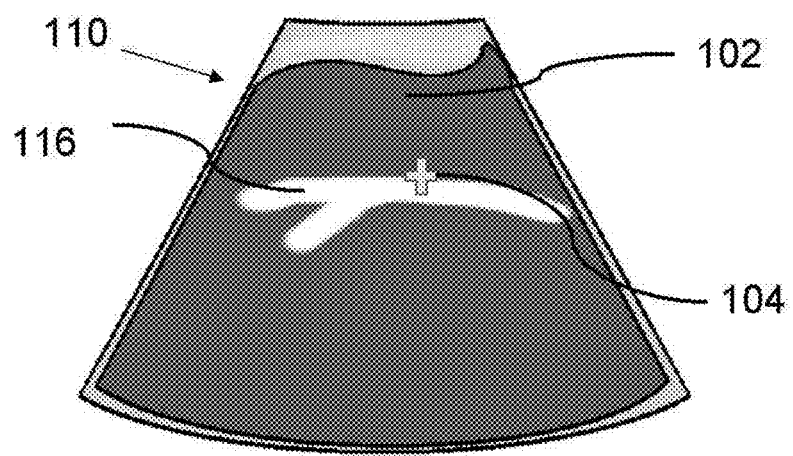
FIG. 6 is another ultrasound image of tissue to be examined to determine fractional fat content together with reference tissue and showing a region of interest encompassing the tissue to be examined and the reference tissue.

FIG. 6 shows an ultrasound B-mode image 110 in which the portal vein 116 is prominent through the liver 102 of the subject S. Region of interest 104 is shown encompassing a portion of the subject's liver 102 that is to be examined to determine fractional fat content. The region of interest 104 also encompasses a portion of the portal vein 116 (reference tissue) from which the reference thermoacoustic measurement value $M_{ref}$ can be generated.

Turning back to FIG. 3, at step 407, a fractional fat content matrix or map $[\eta_{tissue}]$ of target tissue within the region of interest ROI is determined using the normalized thermoacoustic measurement matrix $[M_{tissue}]$ and the reference thermoacoustic measurement value $M_{ref}$. The fractional fat content map $[\eta_{tissue}]$ can be determined in a variety of ways. Three (3) techniques of determining the fractional fat content map $[\eta_{tissue}]$ using the normalized thermoacoustic measurement matrix $[M_{tissue}]$, and the reference thermoacoustic measurement value $M_{ref}$ will now be described with reference to FIGS. 7 to 11.

The techniques for determining the fractional fat content map $[\eta_{tissue}]$ described below require thermoacoustic measurements from the tissue within the region of interest ROI for which a fractional fat content measurement is required (for example the liver), and a reference thermoacoustic measurement from tissue known to be lean. Ideally, the reference thermoacoustic measurement value $M_{ref}$ is derived from the same tissue type as the tissue from which the normalized thermoacoustic measurement matrix $[M_{tissue}]$ is derived (or tissue with comparable thermoacoustic properties). However, this may be impractical in the case of liver tissue, since it may not be known a priori if a certain part of the liver has no fat infiltration. Alternately, the reference thermoacoustic measurement value $M_{ref}$ can be taken from other tissue known to be lean (kidney, portal vein, or gallbladder bile for example).

Tissue with a higher fractional fat content will have different dielectric and thermal properties compared to lean (no fat content) tissue. Thus, the fractional fat content in the region of interest ROI can be deduced from thermoacoustic measurements.

The thermoacoustic signal Sig(r) generated at a tissue location r can be expressed as:

$$Sig(r) = \frac{\beta \cdot v^2}{C_p} H(r) \quad \text{(Eq. 1)}$$

where $\beta$ is the thermal coefficient of expansion, v is the speed of sound in the medium, $C_p$ is the specific heat capacity and H(r) is the absorbed energy density, which is dominated by the dielectric permittivity of the medium at the microwave frequency of thermoacoustic excitation.

Figure 7:
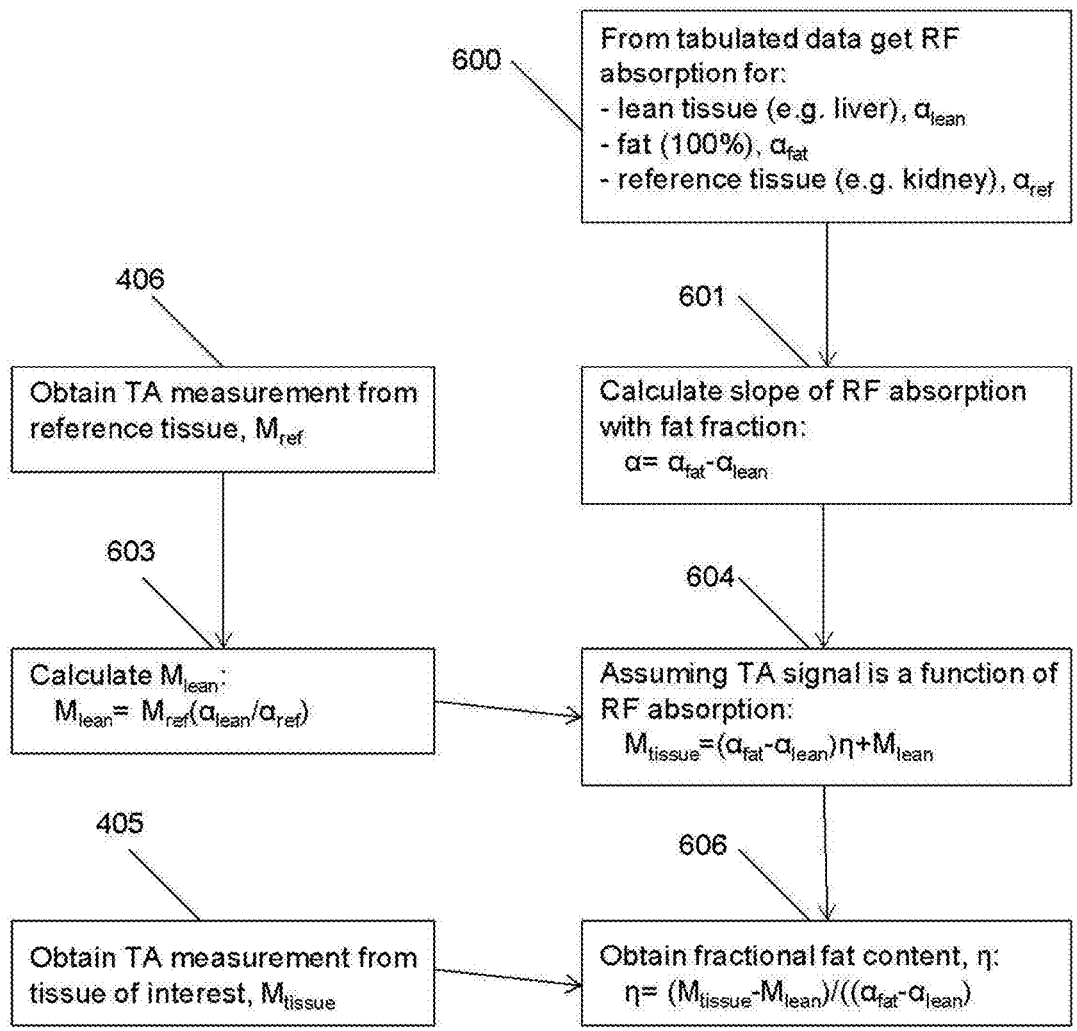
FIG. 7 is a flowchart showing steps for calculating a fractional fat content map.
Figure 8:
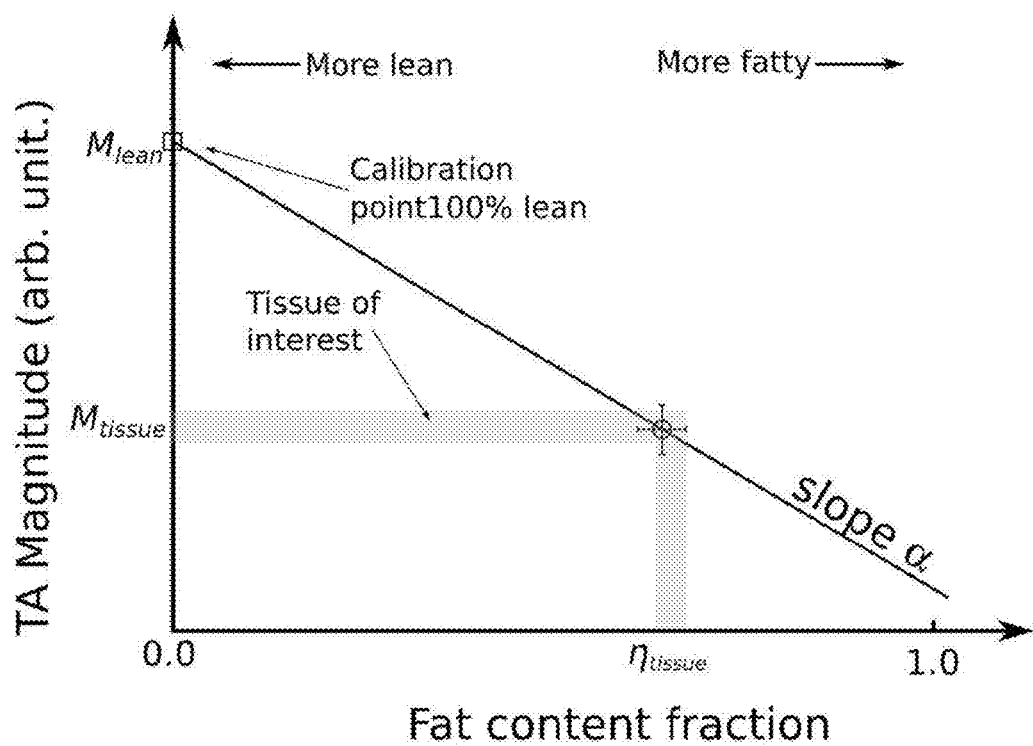
FIG. 8 is a graph showing fractional fat content vs. thermoacoustic data magnitude.

Turing now to FIG. 7, a first technique for determining the fractional fat content map $[\eta_{tissue}]$ at step 407 is shown. In this embodiment, it is assumed that the thermal coefficient of expansion and the specific heat from Eq. 1 vary weakly with fat content. Thus, the dominant parameter affecting the thermnoacoustic signal Sig(r) is the energy absorption density, which, in turn, is proportional to the RF absorption coefficient $\alpha(r)$:

$$Sig(r) \propto \alpha(r) \quad \text{[Eq. 2]}$$

It is also assumed that the ratio of a measured thermoacoustic signal from lean tissue ($M_{lean}$) to that from fatty tissue ($M_{tissue}$) is equal to the ratio of the RF absorption coefficients of the lean tissue to fatty tissue, respectively. More generally, it follows that the thermoacoustic measurement value $M_{tissue}$ from a given tissue varies linearly with fractional fat content $\eta_{tissue}$, with a slope $\alpha$ equal to $\alpha_{fat} - \alpha_{lean}$ (see FIG. 8). As will be appreciated, the slope $\alpha$ is a negative quantity since the RF absorption in water-rich lean tissue is almost 1 order of magnitude higher than the RF absorption in fat. Thus, the thermoacoustic measurement value $M_{tissue}$ can be expressed as:

$$M_{tissue} = \alpha \eta_{tissue} + M_{lean} \quad \text{[Eq. 3]}$$

Thus, by taking a reference thermoacoustic measurement value from lean tissue of the same type, and thermoacoustic measurement values $M_{tissue}$ from the target tissue in the region of interest ROI selected at step 400, the fractional fat content of the target tissue in the region of interest ROI selected at step 400 can be calculated.

As mentioned above, it may be difficult to identify reference tissue of the same type as the target tissue within the region of interest ROI selected at step 400, that is also known to be lean. As such, to obtain the reference thermoacoustic measurement value $M_{ref}$, the reference tissue may be selected from another type of tissue that is known to have no fat content. Examples of types of tissue mentioned above that are known to have no or very little fat content include the kidney, portal vein and the galbladder bile. Since the reference tissue may have different thermnnoacoustic properties (namely thermoacoustic absorption) to that of the tissue of interest (liver for instance), it is necessary to calculate a corrected reference thermoacoustic reference value $M_{lean}$ (step 603) according to:

$$M_{lean} = M_{ref} \cdot \alpha_{lean}/\alpha_{ref} \quad \text{[Eq. 4]}$$

where $\alpha_{lean}$ and $\alpha_{ref}$ are the RF absorption values for normal lean tissue and for the reference tissue, respectively. The RF absorption values are readily obtained from tabulated data for RF frequencies of interest [Gabriel 1996] (step 600).

The slope $\alpha$ of the RF absorption values $\alpha_{fat}$ and $\alpha_{lean}$ is then calculated according to $\alpha = \alpha_{fat} - \alpha_{lean}$ (step 601). Assuming each thermoacoustic measurement value is proportional to RF absorption, at step 604 the thermoacoustic measurement value $M_{tissue}$ can be expressed as:

$$M_{tissue} = (\alpha_{fat} - \alpha_{lean})\eta + M_{lean} \quad \text{[Eq. 5]}$$

Therefore, for each thermoacoustic measurement value $M_{tissue}$ in the normalized thermoacoustic measurement matrix $[M_{tissue}]$, a fractional fat content value n can be calculated at step 606 according to:

$$\eta = (M_{tissue} - M_{lean})/(\alpha_{fat} - \alpha_{lean}) \quad \text{[Eq. 6]}$$

With the fractional fat content values q calculated for the thermoacoustic measurement values $M_{tissue}$, the fractional fat content map $[\eta_{tissue}]$ is generated.

Figure 9:
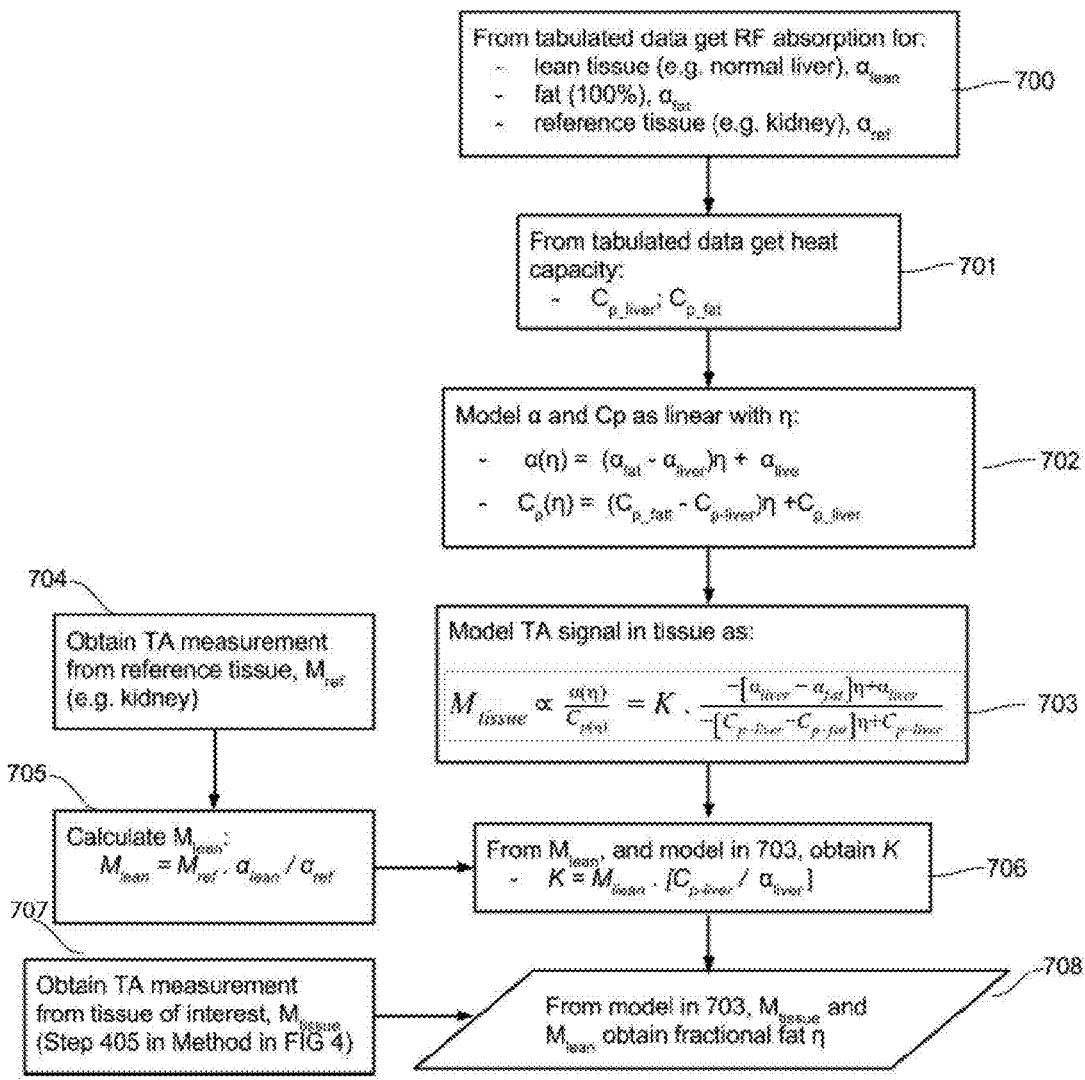
FIG. 9 is a flowchart showing alternative steps for calculating a fractional fat content map.

Another technique to determine the fractional fat content map $[\eta_{tissue}]$ at step 407 is shown in FIG. 9. In this embodiment, a generalized form of Eq. 1 is used as a model to infer fractional fat content. In addition to the fat-fraction-dependent absorption coefficient $\alpha(r)$, the tissue heat capacity $C_p$ is also assumed to depend on fractional fat content. Specifically, the tissue heat capacity $C_p$ is assumed to be a linear combination of heat capacity in fat and liver tissue (by composition). Thus, in this embodiment, both the tissue heat capacity $C_p$ and absorbed energy density H(r) vary linearly with fractional fat content and, for the case of a region of interest within the liver, at step 703 the thermoacoustic measurement value $M_{tissue}$ from a fatty liver can be expressed as:

$$M_{tissue} \propto \frac{\alpha(\eta)}{C_{p(\eta)}} = K \frac{-[\alpha_{liver} - \alpha_{fat}]\eta + \alpha_{liver}}{-[C_{p\text{-}liver} - C_{p\text{-}fat}]\eta + C_{p\text{-}liver}} \quad [\text{Eq. 7}]$$

where $\eta$ is the fractional fat content of tissue of interest, which in this example is the liver, $\alpha_{liver}$ and $\alpha_{fat}$ are the RF absorption values for liver tissue and fat, respectively, $C_{p\text{-}liver}$ and $C_{p\text{-}fat}$ are the heat capacity for liver and fat, respectively, obtained from tabulated data and K is a constant value.

The absorption coefficient $\alpha(\eta)$ is expressed as $\alpha(\eta) = (\alpha_{fat} - \alpha_{lean})\eta + \alpha_{liver}$, and the heat capacity $C_p(\eta)$ is expressed as $(C_{p\text{-}fat} - C_{p\text{-}liver})\eta + C_{p\text{-}liver}$ (step 702).

For normal (lean) liver tissue ($\eta=0$) and thus, Eq. 7 yields:

$$K = M_{lean}\left[\frac{C_{p\text{-}liver}}{\alpha_{liver}}\right] \quad [\text{Eq. 8}]$$

As mentioned above, it may be difficult to identify reference tissue of the same type as the target tissue within the region of interest ROI selected at step 400, that is also known to be lean. As such, to obtain the reference thermoacoustic measurement value $M_{ref}$, the reference tissue mentioned above may be selected from another type of tissue that is known to have no fat content. Examples of types of tissue that are known to have no or very little fat content include the kidney, portal vein and the galbladder bile. Since the reference tissue may have different thermoacoustic properties (namely thermoacoustic absorption) to that of the tissue of interest (liver for instance), it is necessary to calculate a corrected reference thermoacoustic reference value $M_{lean}$ (step 706) according to:

$$M_{lean} = M_{ref}\alpha_{lean}/\alpha_{ref} \quad [\text{Eq. 9}]$$

where $\alpha_{lean}$ and $\alpha_{ref}$ are the RF absorption values for normal lean liver tissue and for the reference tissue, respectively.

Figure 10:
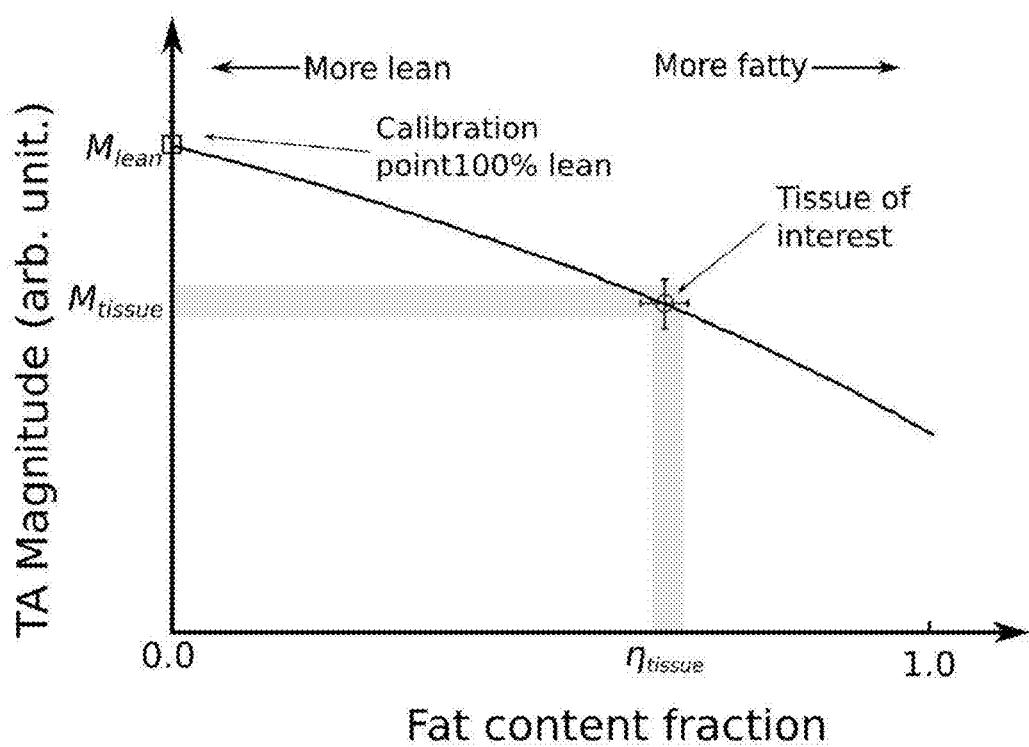
FIG. 10 is another graph showing fractional fat content vs. thermoacoustic data magnitude.

The fractional fat content map $[\eta_{tissue}]$ is calculated by solving Eqs. 7, 8 and 9 using the appropriate tabulated RF absorption coefficients (for fat, normal liver tissue and reference tissue) and tabulated heat capacity coefficients (for normal liver tissue and fat) (steps 700 and 701), the thermoacoustic measurement values $M_{tissue}$ of the normalized thermoacoustic measurement matrix $[M_{tissue}]$ and the reference thermoacoustic value $M_{ref}$ (step 708 and FIG. 10).

Figure 11:
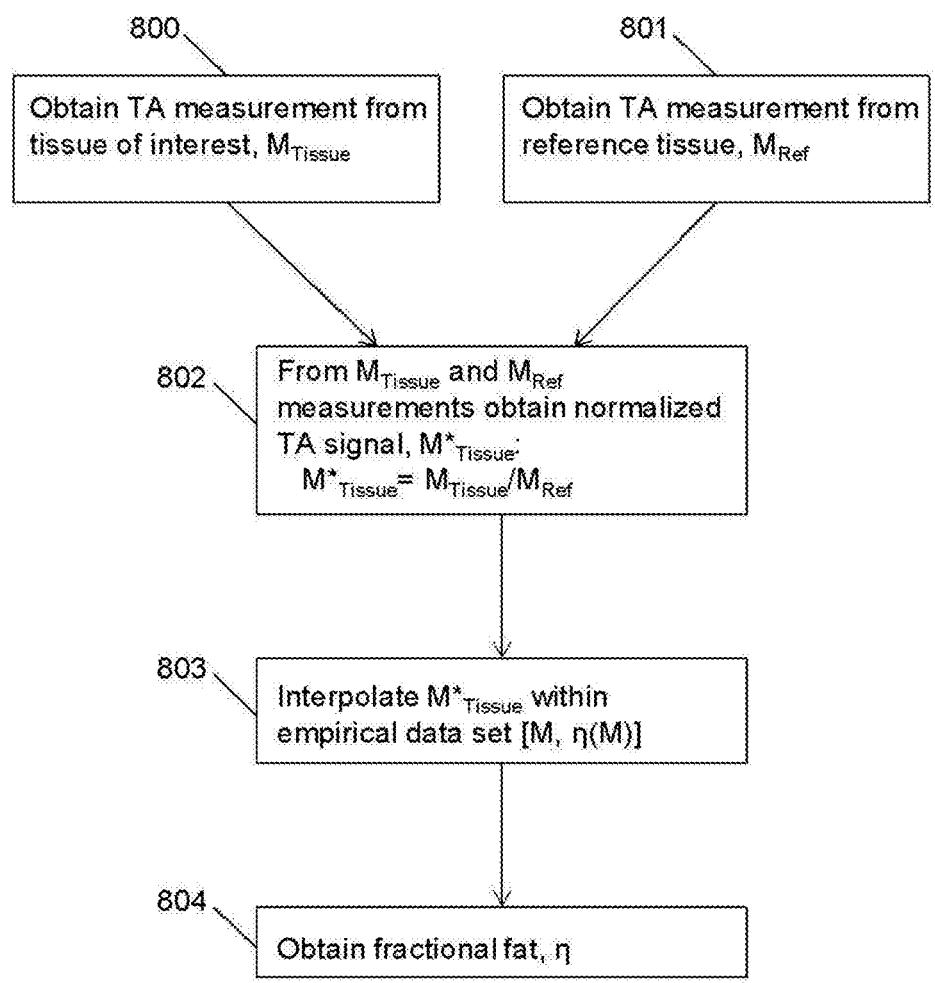
FIG. 11 is a flowchart showing alternative steps for calculating a fractional fat content map.

Another technique to determine the fractional fat content map $[\eta_{tissue}]$ at step 407 is shown in FIG. 11. In this embodiment, the fractional fat content map $[\eta_{tissue}]$ is determined from the thermoacoustic measurement values $M_{tissue}$ of the normalized thermoacoustic measurement matrix $[M_{tissue}]$ by comparing them to previously-generated and tabulated data that maps fractional fat content to thermoacoustic measurements for that particular tissue type (e.g. liver tissue).

The tabulated data is obtained by taking thermoacoustic measurements of various samples of tissue-mimicking phantoms with different fractional fat content similar to the experiment in reference [Bauer 2012]. The tissue phantom properties are selected to simulate tissue RF absorption as well as thermal properties. Additionally, the tissue phantom could be maintained at 37° C. to simulate in vivo imaging.

In one embodiment, the tabulated data is obtained by collecting and analyzing a large data set of thermoacoustic images from patients for whom gold-standard fractional fat measurements are available. These gold standard measurements could be either from a well characterized imaging modality (e.g. magnitude-based MRI [Schwimmer 2015] or CT imaging) or from pathology analysis of biopsy samples from the imaged tissues. A method for generating a function, $\eta(M)$, that gives the fractional fat content for a given a normalized thermoacoustic measurement value $M_{tissue'}$ will now be described.

In this embodiment, at step 802 each thermoacoustic measurement $M_{tissue}$ of the normalized thermoacoustic measurement matrix $[M_{tissue}]$ is normalized according to:

$$M_{tissue'} = \frac{M_{tissue}}{M_{ref}} \quad [\text{Eq. 10}]$$

where $M_{tissue'}$ is the normalized thermoacoustic measurement value.

For each normalized thermoacoustic measurement $M_{tissue'}$ the fractional fat content value $\eta_{tissue}$ is obtained by interpolating to the empirically-obtained data $[M, \eta(M)]$ (step 803). The fractional fat content values $\eta_{tissue}$ can then be used to create the fractional fat content map $[\eta_{tissue}]$.

As will be appreciated, this embodiment requires a robust set of data points comprising gold-standard tissue fractional fat content measurements and corresponding thermoacoustic measurements, for a given tissue type (e.g. liver). The goldetandard fractional fat content measurements may be derived from a histo-pathology, MRI or CT imaging. The thermoacoustic measurements are calibrated for the incident RF power, ultrasonic transducer sensitivity, acceptance angle, and other parameters.

In another embodiment, the data set may be collected during a clinical study where a statistically-significant number of subjects are used to obtain a non-invasive thermoacoustic measurement of the tissue of interest and a gold standard fractional-fat content assessment of that same tissue.

After the fractional fat content map $[\eta_{tissue}]$ has been generated at step 407, the fractional fat content map $[\eta_{tissue}]$ is used to yield a corrected, normalized thermoacoustic measurement matrix $[M_{tissue}]$ (step 408) that is fed back to step 407 so that a corrected fractional fat content map $[\eta_{tissue}]$ can be generated. This process is performed iteratively until a final fractional fat content map is generated at step 409.

The steps performed to yield the corrected, normalized thermoacoustic measurement matrix $[M_{tissue}]$ (step 408) will now be described. Initially, a lookup table that relates fractional fat content q to corresponding speed of sound is accessed. The lookup table is generated based on experimental, theoretical or empirical published data. The experimental or theoretical data can be linked to existing studies of fractional fat content performed using acceptable methods, including but not limited to, MRI, ultrasound imaging, or biopsies. Alternatively, a manufactured phantom that simulates different types of tissue can be used to determine the relationships between fractional fat content and corresponding speed of sound. The lookup table data is then used to correct each thermoacoustic measurement value $M_{tissue}$ in the normalized thermoacoustic measurement matrix $[M_{tissue}]$ for the speed-of-sound dependence of the voxed volume to yield the corrected, normalized thermoacoustic measurement matrix [$M_{tissue}$] that is fed back to step 407.

In particular, each thermoacoustic measurement value $M_{tissue}$ in the normalized thermoacoustic measurement matrix [$M_{tissue}$] is scaled by the term $[v_{tissue}/v_{lean}]^3$ where $v_{lean}$ is the speed of sound of the reference tissue and $v_{tissue}$ is the speed of sound of the target tissue from which each thermoacoustic measurement value $M_{tissue}$ is derived. For the first iteration the speed of sound $v_{tissue}$ is assumed to be 1540 m/s, which is the default speed of sound in tissue used by commercial ultrasound systems, and the speed of $v_{lean}$ is derived from the lookup table.

After the first iteration, when the corrected, normalized thermoacoustic measurement matrix [$M_{tissue}$] is returned to step 407 and a corrected fractional fat content map [$\eta_{tissue}$] is generated, at step 408 the speed of sound values for the corrected thermoacoustic measurement values $M_{tissue}$ are derived from the lookup table.

The number of times the iterations are performed can vary. For example, the iterations can be performed a fixed number of times, such as twice, before the final fractional fat content map is deemed to have been generated at step 409. Alternatively, the number of iterations can be performed until the change in certain value(s) from one iteration to the next falls below a threshold. For example, if the change in the speed of sound $v_{tissue}$ falls below 10% from one iteration to the next, the final fractional fat content map can be deemed to have been generated at step 409. Alternatively, if the change in the thermoacoustic measurement values of the corrected, normalized thermoacoustic measurement matrix [$M_{tissue}$] from one iteration to the next falls below a threshold, the final fractional fat content map can be deemed to have been generated at step 409.

Figure 12:
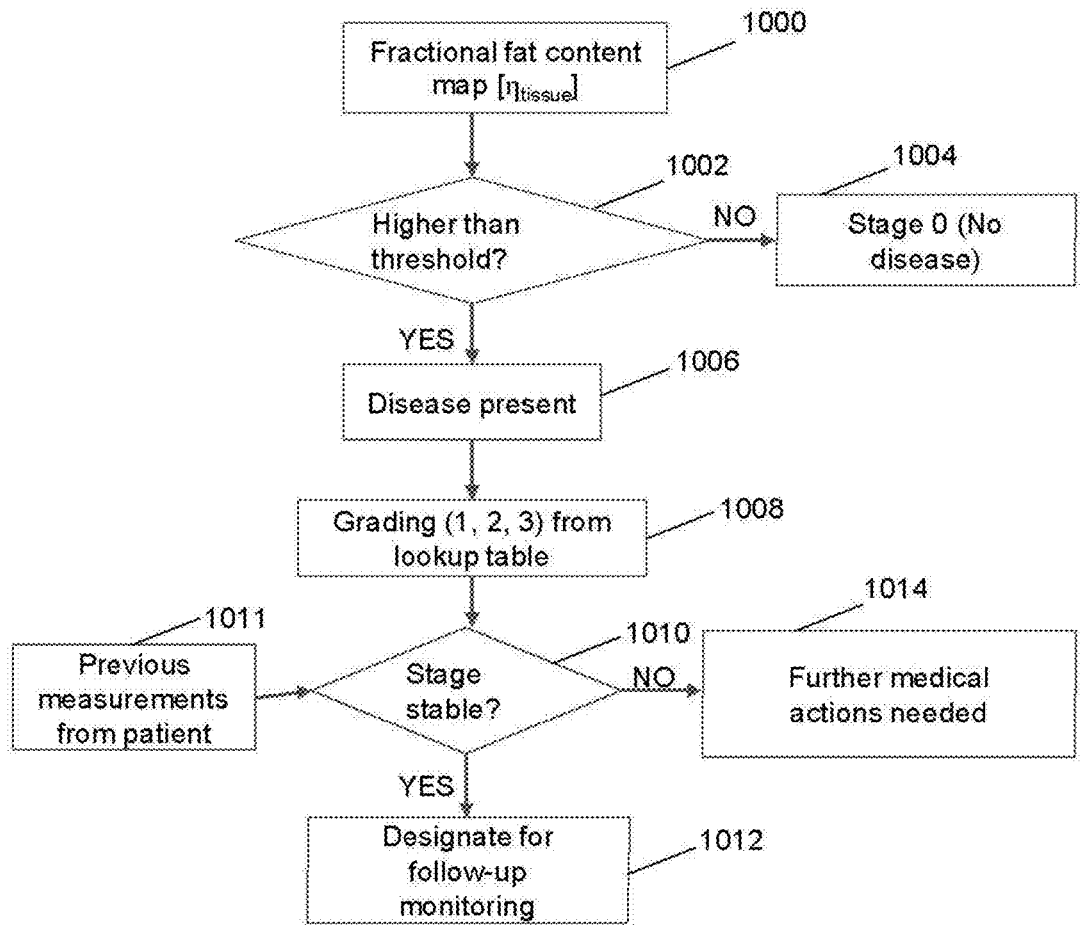
FIG. 12 is a flowchart showing steps for grading tissue.

Once the final fractional fat content map [$\eta_{tissue}$] has been generated at step 409, the final fractional fat content map [$\eta_{tissue}$] can be used to grade the target tissue within the region of interest ROI selected at step 400 as shown in FIG. 12. Initially, the fractional fat content map [$\eta_{tissue}$] (step 1000) is compared to a threshold (step 1002). During this step, the fractional fat content values in the final fractional fat content map [$\eta_{tissue}$] can be averaged to yield a single fractional fat content value that is compared to the threshold or individual fractional fat content values in the final fractional fat content map [$\eta_{tissue}$] can be compared to the threshold. In this embodiment, the threshold is for fatty liver disease and is set at a fractional fat content of 5%. In other embodiments, the threshold can be set anywhere from 3% to 40%.

If the fractional fat content value(s) $\eta_{tissue}$ is/are less than the threshold, it is determined that the subject does not have a disease and thus, the target tissue within the region of interest ROI is graded as a zero (0) (step 1004). If the fractional fat content value(s) $\eta_{tissue}$ is/are higher than the threshold, it is determined that a disease such as steatosis is present (step 1006). The target tissue within the region of interest ROI is in turn graded as a one (1), two (2) or three (3) by comparing the fractional fat content value(s) $\eta_{tissue}$ to known tabulated values (step 1008). In this embodiment, the known tabulated values are outlined in "Non-alcoholic steatohepatitis: A proposal for grading and staging the histological lesions," authored by Brunt at al., Am. J. Gastroenterol., vol. 94, no. 9, pp. 2467-2474, September 1999.

Specifically, in this embodiment, the target tissue within the region of interest ROI is graded as a one (1) if the estimated fractional fat content is between 5% and 33%. The target tissue within the region of interest ROI is graded as a two (2) if the estimated fractional fat content is between 34% and 66%. The target tissue within the region of interest ROI is graded as a three (3) if the estimated fractional fat content is greater than 66%.

The grade of the target tissue within the region of interest ROI is then compared to previous grades obtained for the subject (if available) (step 1010). If the grade of the target tissue has not changed, the target tissue is deemed stable and the subject is distinguished for follow up monitoring (step 1012). If the grade of the target tissue has changed, further medical actions are deemed to be required (step 1014).

Those skilled in the art will appreciate that various tissue of interest may be evaluated such as for example the heart, kidney(s), lung, esophagus, thymus, breast, prostate, brain, muscle, nervous tissue, epithelial tissue, bladder, gallbladder, intestine, liver, pancreas, spleen, stomach, testes, ovaries, uterus, skin and adipose tissues.

Although embodiments have been described above with reference to the accompanying drawings, those of skill in the art will appreciate that variations and modifications may be made without departing from the scope thereof as defined by the appended claims.

What is claimed is:

1. A method for determining fractional fat content of tissue comprising:
    registering thermoacoustic image coordinates to an acquired ultrasound image, the acquired ultrasound image at least comprising target tissue within a region of interest;
    defining a thermoacoustic voxel grid coincident with the region of interest;
    obtaining thermoacoustic image measurement values from tissue within the region of interest corresponding to the voxels within the defined thermoacoustic voxel grid to yield a thermoecoustic measurement matrix;
    normalizing the thermoacoustic image measurement values within the thermoacoustic measurement matrix;
    calculating a fractional fat content map for the target tissue within the region of interest based on the normalized thermoacoustic image measurement values within the thermoacoustic measurement matrix and a reference thermoacoustic measurement value; and
    correcting the fractional fat content map based on tissue speed-of-sound data to yield a final fractional fat content map for the target tissue within the region of interest.

2. The method of claim 1, wherein the calculating and correcting are performed iteratively.

3. The method of claim 2, wherein during the correcting a corrected thermoacoustic measurement matrix is generated based on the tissue speed-of-sound data, wherein the corrected thermoacoustic measurement matrix and the reference thermoacoustic measurement value are used to recalculate the fractional fat content map, and wherein the above steps are repeated until the final fractional fat content map for the target tissue is generated.

4. The method of claim 3, wherein the calculating and correcting are performed iteratively a threshold number of times or until the change in one or more values from one iteration to the next falls below a threshold.

5. The method of claim 3, wherein the reference thermoacoustic measurement value is derived from lean tissue as compared to the target tissue.

6. The method of claim 5, wherein the target tissue within the region of interest is one of liver tissue, pancreatic tissue, muscle tissue, lung tissue and heart tissue and wherein the lean tissue is one of kidney tissue, portal vein tissue and gallbladder bile.

7. The method of claim 5, wherein the corrected thermoacoustic measurement matrix is generated by scaling the thermoacoustic measurement values within the thermoacoustic measurement matrix by a cubed ratio, and wherein the ratio is the speed of sound in the reference tissue divided by the speed of sound in the target tissue.

8. The method of claim 5, wherein calculating the fractional fat content map is further based on energy absorption values of the target tissue and the reference tissue.

9. The method of claim 8, wherein calculating the fractional fat content map is further based on heat capacity of the target tissue and the reference tissue.

10. The method of claim 5, wherein calculating the fractional fat content map is based on a comparison of previously-generated data that maps fractional fat content to thermoacoustic measurements for the target tissue.

11. The method of claim 1, wherein during the normalizing the thermoacoustic measurement values within the thermoacoustic measurement matrix are normalized as a function of radio frequency energy, attenuation and the number of voxels in the thermoacoustic voxel grid.

12. The method of claim 1, further comprising using an ultrasound imaging system to acquire the ultrasound image and delineating the region of interest on the acquired ultrasound image.

13. The method of claim 12, wherein the delineated region of interest encompasses the target tissue and reference tissue from which the reference thermoacoustic measurement value is derived.

14. The method of claim 1 further comprising using the final fractional fat content map to grade the target tissue.

15. An apparatus comprising:
a thermoacoustic imaging system configured to acquire thermoacoustic image data of target tissue within a region of interest; and
one or more processors configured to:
register coordinates of the thermoacoustic image data to an acquired ultrasound image, the acquired ultrasound image comprising the target tissue;
define a thermoacoustic voxel grid coincident with the region of interest;
generate from the thermoacoustic image data, a thermoacoustic measurement matrix comprising thermoacoustic measurement values that correspond to the voxels within the defined thermoacoustic voxel grid;
normalize the thermoacoustic image measurement values within the thermoacoustic measurement matrix;
calculate a fractional fat content map for the target tissue within the region of interest based on the normalized thermoacoustic image measurement values within the thermoacoustic measurement matrix and a reference thermoacoustic measurement value; and
correct the fractional fat content map based on tissue speed-of-sound data to yield a final fractional fat content map for the target tissue within the region of interest.

16. The apparatus of claim 15, wherein the one or more processors are configured to, during the correcting, generate a corrected thermoacoustic measurement matrix based on the tissue speed-of-sound data, and use the corrected thermoacoustic measurement matrix and the reference thermoacoustic measurement value to recalculate the fractional fat content map, and wherein the one or more processors are configured to perform the above steps iteratively until the final fractional content map of the target tissue is generated.

17. The apparatus of claim 16, wherein the one or more processors are configured to perform the calculating and correcting iteratively a threshold number of times or until the change in one or more values from one iteration to the next falls below a threshold.

18. The apparatus of claim 17, wherein the reference thermoacoustic measurement value is derived from lean tissue as compared to the target tissue.

19. The apparatus of claim 18, wherein the corrected thermoacoustic measurement matrix is generated by scaling the thermoacoustic measurement values within the thermoacoustic measurement matrix by a cubed ratio, and wherein the ratio is the speed of sound in the reference tissue divided by the speed of sound in the target tissue.

20. The apparatus of claim 15, further comprising an ultrasound imaging system configured to acquire the ultrasound image, wherein the one or more processors are configured to delineate the region of interest on the acquired ultrasound image and wherein the delineated region of interest encompasses the target tissue and reference tissue from which the reference thermoacoustic measurement value is derived.

* * * * *